(12) United States Patent
Meridew et al.

(10) Patent No.: US 9,744,046 B2
(45) Date of Patent: Aug. 29, 2017

(54) LOCKING SCREW ASSEMBLY

(71) Applicant: Biomet Manufacturing, LLC, Warsaw, IN (US)

(72) Inventors: Jason D. Meridew, Warsaw, IN (US); W. Jason Slone, Silver Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 187 days.

(21) Appl. No.: 13/754,239

(22) Filed: Jan. 30, 2013

(65) Prior Publication Data

US 2013/0204388 A1 Aug. 8, 2013

Related U.S. Application Data

(60) Provisional application No. 61/595,924, filed on Feb. 7, 2012.

(51) Int. Cl.
*A61F 2/34* (2006.01)
*A61B 17/86* (2006.01)
*A61F 2/30* (2006.01)

(52) U.S. Cl.
CPC .............. *A61F 2/34* (2013.01); *A61B 17/86* (2013.01); *A61F 2002/30387* (2013.01); *A61F 2002/30777* (2013.01); *A61F 2002/3403* (2013.01)

(58) Field of Classification Search
CPC ..................................... A61F 2/32; A61F 2/38
USPC ... 623/20.35, 20.36, 22.11–22.2, 22.4–23.14
See application file for complete search history.

(56) References Cited

U.S. PATENT DOCUMENTS

| | | | |
|---|---|---|---|
| 5,725,588 A | 3/1998 | Errico et al. | |
| 5,888,204 A | 3/1999 | Ralph et al. | |
| 6,228,121 B1* | 5/2001 | Khalili | 623/22.36 |
| 6,454,769 B2 | 9/2002 | Wagner et al. | |
| 7,316,715 B2 | 1/2008 | Plaskon | |
| 2003/0078583 A1 | 4/2003 | Biedermann et al. | |
| 2004/0127900 A1 | 7/2004 | Konieczynski et al. | |
| 2007/0250175 A1 | 10/2007 | Meridew et al. | |
| 2008/0243261 A1* | 10/2008 | Wyss et al. | 623/20.33 |
| 2009/0204225 A1 | 8/2009 | Meridew et al. | |
| 2009/0210067 A1* | 8/2009 | Meridew | 623/22.24 |

\* cited by examiner

*Primary Examiner* — Yashita Sharma
(74) *Attorney, Agent, or Firm* — Schwegman Lundberg & Woessner, P.A.

(57) ABSTRACT

An acetabular implant including an acetabular cup having a wall with a first elongated slot defining a passage through the wall, and an insert slidably received in the first elongated slot and movable relative to the slot in a first direction. The insert can include a second elongated slot that extends in a second direction different than the first direction. The second elongated slot can be configured to slidably receive a bone fastener and guide the bone fastener through the passage of the acetabular cup at a selected angle.

19 Claims, 5 Drawing Sheets

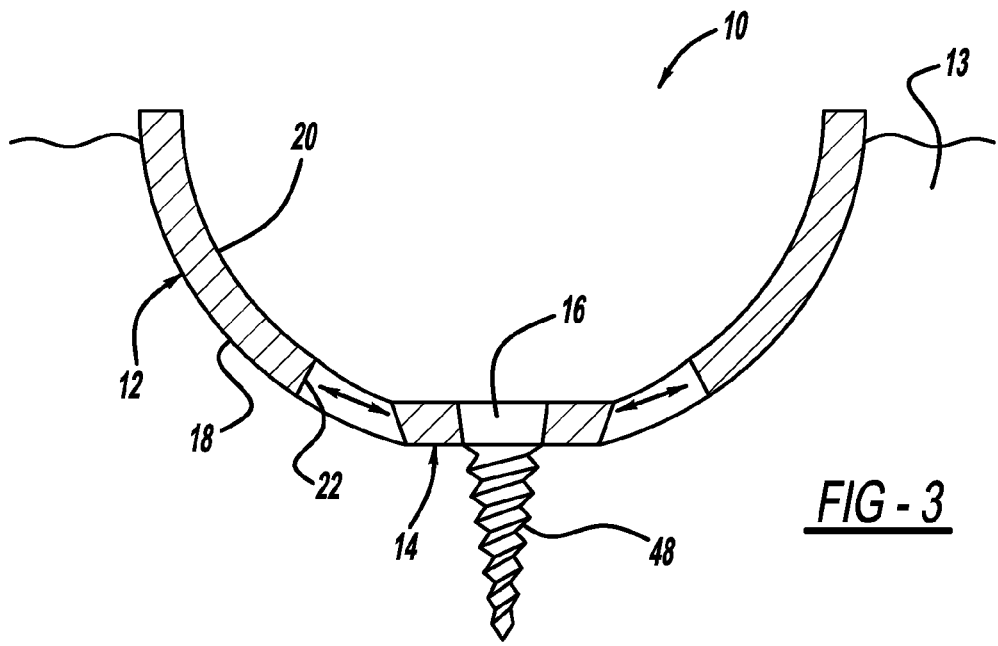
FIG - 3
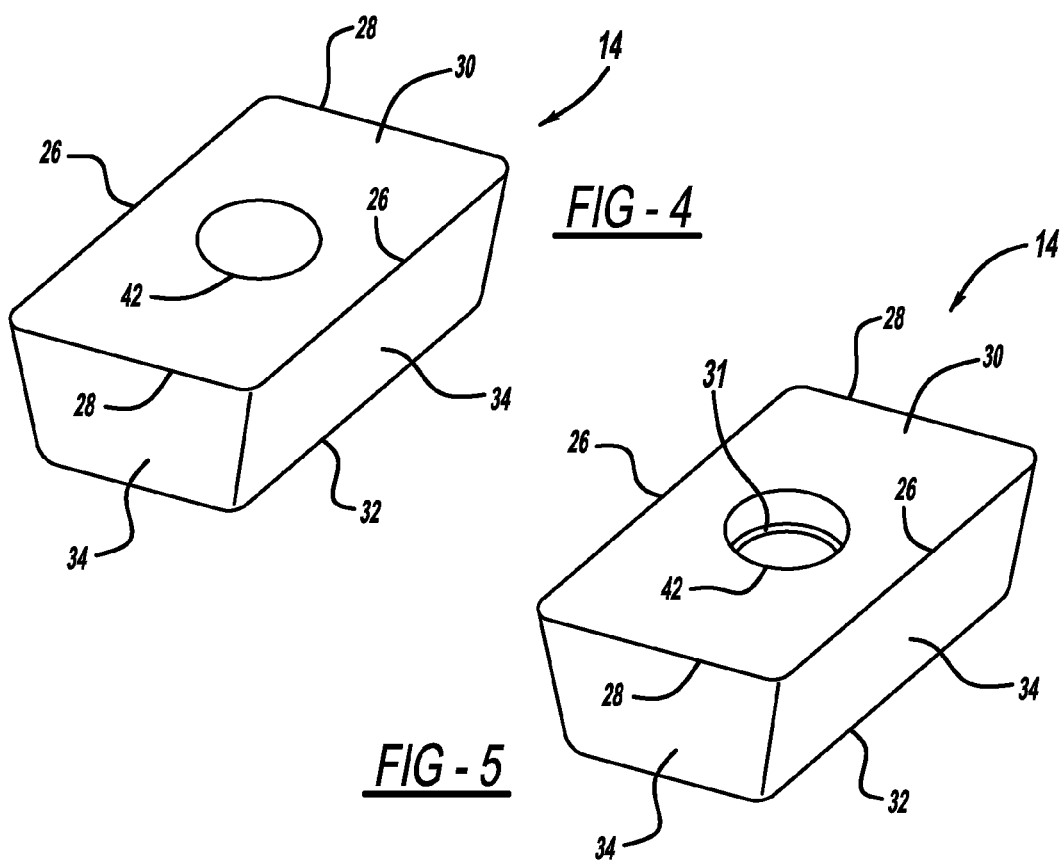
FIG - 4
FIG - 5

LOCKING SCREW ASSEMBLY

CROSS-REFERENCE TO RELATED APPLICATIONS

This application claims the benefit of U.S. Provisional Application No. 61/595,924, filed Feb. 7, 2012. The entire disclosure of the above application is incorporated herein by reference.

FIELD

The present disclosure relates to a locking screw assembly for an acetabular cup.

BACKGROUND

This section provides background information related to the present disclosure which is not necessarily prior art.

A hip joint comprises a socket or acetabulum and a femoral head or ball received in the acetabulum. The hip joint, therefore, is a ball and socket joint that provides universal motion. Various diseases, such as osteoarthritis, may attack the hip joint. When this occurs, it may be necessary to utilize an appropriate hip joint prosthesis to replace the femoral head and the acetabulum. This may also be necessary in other circumstances, such as, for example, certain hip joint fractures.

Deterioration of the acetabulum requires that an acetabular cup be mounted in the acetabulum to provide a socket for slidably receiving the prosthetic femoral head. In general, the acetabular cup is cemented in the acetabulum or secured in the acetabulum by other means. Regardless, the acetabular cup should be securely mounted within the acetabulum to ensure proper alignment and fixation of the acetabular cup. If it is not and misalignment of undesired movement occurs, additional surgery may be required to correct the problem.

SUMMARY

This section provides a general summary of the disclosure, and is not a comprehensive disclosure of its full scope or all of its features.

The present disclosure provides an acetabular implant. The acetabular implant can include an acetabular cup having a wall with a first elongated slot defining a passage through the wall, and an insert slidably received in the first elongated slot and movable relative to the slot in a first direction. The insert can include a second elongated slot that extends in a second direction different than the first direction. The second elongated slot can be configured to slidably receive a bone fastener and guide the bone fastener through the passage of the acetabular cup at a selected angle.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 3 is a cross-sectional view of an acetabular implant according to various principles of the present disclosure;

FIG. 4 is a perspective view of an insert of an acetabular implant according to various principles of the present disclosure;

FIG. 5 is a perspective view of another insert of an acetabular implant according to various principles of the present disclosure;

Corresponding reference numerals indicate corresponding parts throughout the several views of the drawings.

DETAILED DESCRIPTION

Figure 1:
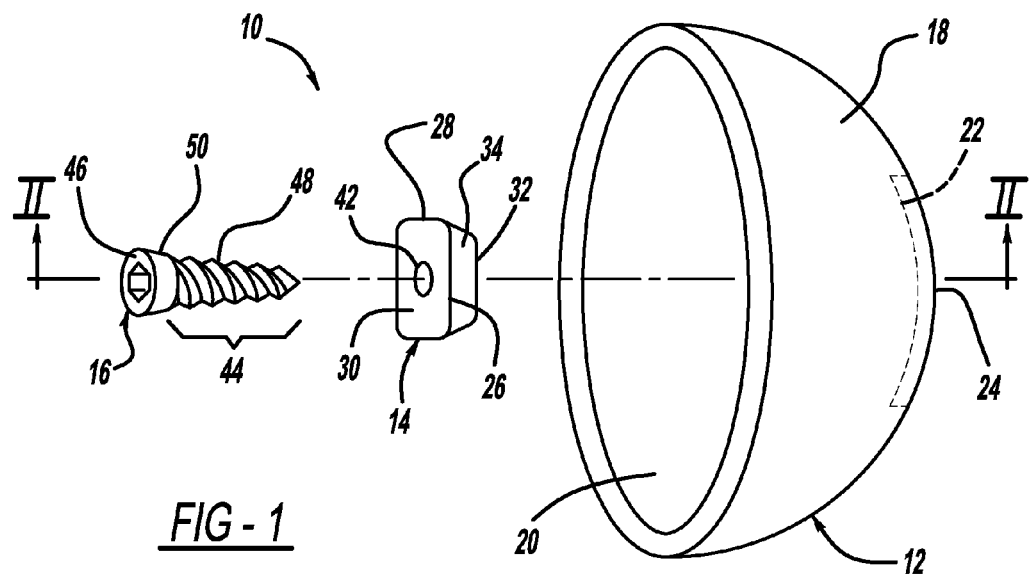
FIG. 1 is an exploded perspective view of an acetabular implant according to various principles of the present disclosure.

Example embodiments will now be described more fully with reference to the accompanying drawings.

FIGS. 1-6 illustrate an exemplary acetabular cup assembly 10 in accordance with the present disclosure. Assembly 10 can include an acetabular cup 12 that can be secured in an acetabulum 13 of a patient as part of a prosthetic hip. To secure acetabular cup 12 in the acetabulum 13 (FIG. 2) of the patient, assembly 10 can also include an insert 14 that can receive a fastener 16.

Acetabular cup 12 can be a hemispherically-shaped member having an exterior surface 18 that can engage with the acetabulum 13 of a patient, and an interior surface 20 that can engage a prosthetic femoral head (not shown) of a prosthetic hip or a natural femoral head. It is understood the acetabular cup 12 may engage the head directly or initially receive a liner between the acetabular cup 12 and the femoral head. Acetabular cup 12 can be formed of a metal material such as titanium, or any other metal material suitable for implantation into a patient that is known to one skilled in the art. In addition, acetabular cup 12 may include a coating or liner (not shown) formed on interior surface 20 made of a polymer material such as polyethylene. Such a liner can improve the lubricity and cushioning characteristics between the prosthetic femoral head (not shown) and acetabular cup 12. As the size of the acetabulum 13 of each patient can vary, a diameter of acetabular cup 12 can also be selected from an appropriate size, such as a range between 40 mm and 80 mm, inclusive.

Acetabular cup 12 can include an aperture 22 that is operable to receive insert 14. Aperture 22 is elongated relative to a length of insert 14, which allows insert 14 to be movable along aperture 22 before insert 14 and acetabular cup 12 are fixed to the acetabulum 13 of the patient by fastener 16. A length of aperture 22 can range between 10 mm and 70 mm, inclusive. Aperture 22 can be formed at a center 24 of acetabular cup 12. The length of the aperture 22 can be defined as an arc length on the surface of the acetabular cup 12. Aperture 22, however, can also be formed at positions radially outward from center 24, without departing from the scope of the present disclosure.

Insert 14 can be a rectangular-shaped member having parallel sides 26 and 28. A length of parallel sides 26 can be about 10 mm, while a length of parallel sides 28 can be about 5 mm. Insert 14 also includes opposing surfaces 30 and 32, with a surface area of surface 30 being greater than a surface area of surface 32. In this regard, opposing surfaces 30 and 32 are connected by sloping sidewalls 34. An angle at which sidewalls 34 slope can be between about 2 degrees to 20 degrees. Aperture 22 can include sloping sidewalls 36 that correspond to sidewalls 34 of insert 14 to ensure proper alignment and engagement between insert 14 and aperture 22. By having sloping sidewalls 34, insert 14 can engage the sloping sidewalls 36 of the aperture 22 without passing entirely through aperture 22.

Insert 14 can be formed of materials such as titanium, or any other material suitable for implantation into a patient that is known to one skilled in the art. In this regard, insert 14 can be formed of the same material as acetabular cup 12, or a material different from that of acetabular cup 12. In addition, similar to acetabular cup 12, insert 14 can be formed to include a coating (not shown) formed of materials such as, for example, polyethylene.

Figure 2:
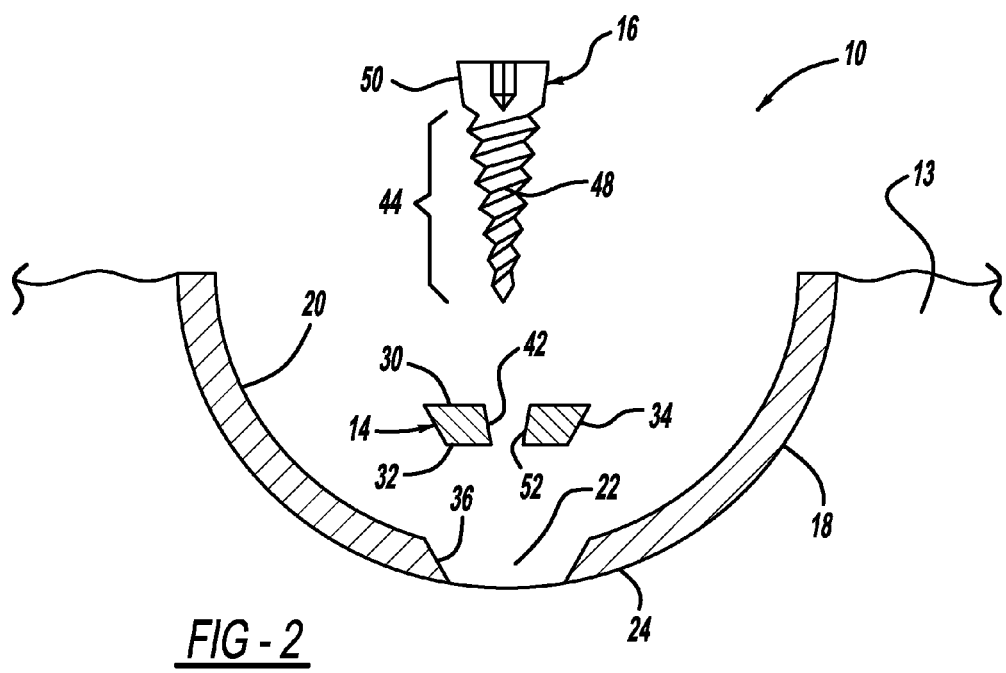
FIG. 2 is an exploded cross-sectional view of an acetabular implant according to various principles of the present disclosure.
Figure 6:
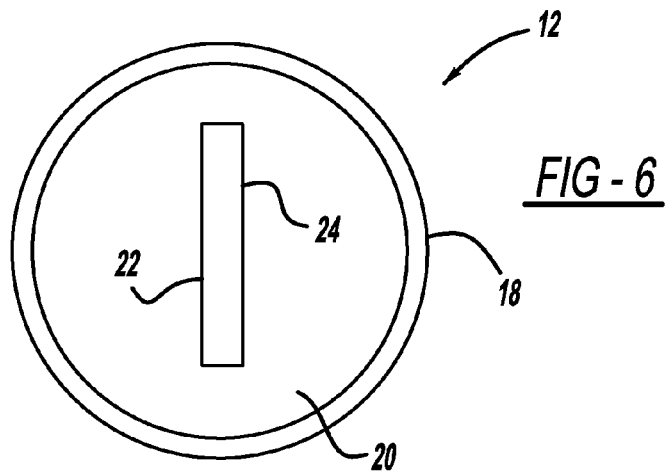
FIG. 6 is perspective view of an acetabular cup of an acetabular implant according to various principles of the present disclosure.

Insert 14 includes a through-hole 42 for receiving fastener 16. Fastener 16 can be a screw having a shank 44 and a head 46. Shank 44 can include a threading 48. Head 46 can include tapered surface 50 for engaging through-hole 42. Alternatively, or in addition to the tapered head 46, if shank 44 includes threading 48, through-hole 42 can include a corresponding threading (not shown) to securely fix fastener 16 to insert 14. As illustrated in FIG. 2, through-hole 42 can include a tapered surface 52 that corresponds to tapered surface 50 of head 46. Alternatively, as shown in FIG. 5, surface 30 can include a recess 31 surrounding through-hole 42. Such a configuration enables use of fasteners including a flat head (not shown). In this regard, through-hole 42 would not have tapered surface 52 because head 46 would engage recess 31.

Fastener 16 can be formed of a material such as, for example, titanium. Although fastener 16 has been described as a bone screw, the present disclosure should not be limited thereto. In this regard, any fastener known to one skilled in the art can be used to secure insert 14 and acetabular cup 12 to the acetabulum 13 of the patient.

To secure acetabular cup 12 to the acetabulum 13 of the patient, acetabular cup 12 is positioned within the acetabulum 13 of the patient. As the condition of the acetabulum 13 can vary from patient to patient, acetabular cup 12 may not necessarily be able to be press-fit within the acetabulum 13 of the patient. In this regard, the bone quality of the acetabulum 13 may have deteriorated to an extent that press-fitting of acetabular cup 12 into the acetabulum 13 is not possible, or is not possible to an extent that ensures that acetabular cup 12 will remain in the acetabulum 13 during the useful life of the acetabular cup 12. Accordingly, in accordance with the present disclosure, acetabular cup 12 includes aperture 22 and insert 14 that allows fastener 16 to be optimally positioned to ensure secure engagement between acetabular cup 12 and the acetabulum 13 of the patient. As discussed, the insert 14 allows the fastener 16 to be positioned in a plurality of orientations per aperture rather than a single or limited orientation.

More particularly, after acetabular cup 12 is positioned in the acetabulum 13 of the patient, insert 14 can then be positioned within aperture 22 of acetabular cup 12. As insert 14 is dimensioned so that it will not pass entirely through aperture 22, insert 14 can then be moved within the aperture 22 to a position that corresponds to the optimal position at which to secure fastener 16 to the acetabulum 13 of the patient. That is, insert 14 can be moved along aperture 22 to a position that best corresponds to an optimum position of the acetabular anatomy where fastener 16 should secure acetabular cup 12 to the acetabulum 13. Once this position is located, fastener 16 may be tightened to secure insert 14 and acetabular cup 12 to the acetabulum 13 of the patient.

As fastener 16 is tightened, sloped sidewalls 34 will securely engage with sloping sidewalls 36 of acetabular cup 12. In addition, tapered surface 50 of the head of fastener 16 will securely engage with tapered surface 52 of through-hole 42. Accordingly, as fastener 16 is fully engaged into the acetabular anatomy of the patient, a tight tolerance between fastener 16, insert 14, and acetabular cup 12 will be achieved, which will prevent or at least substantially minimize movement of acetabular cup 12 within the acetabulum 13 of the patient. Also, the tight interference can resist backout or loosening of the fastener 16.

Figure 7:
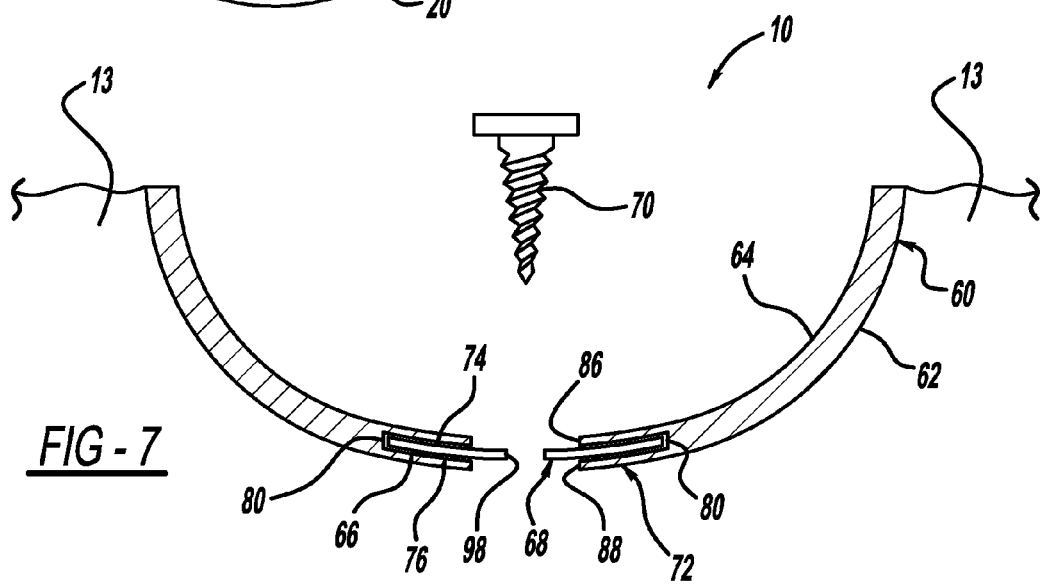
FIG. 7 is a cross-sectional view of an acetabular cup and an insert of an acetabular implant according to various principles of the present disclosure.
Figure 9:
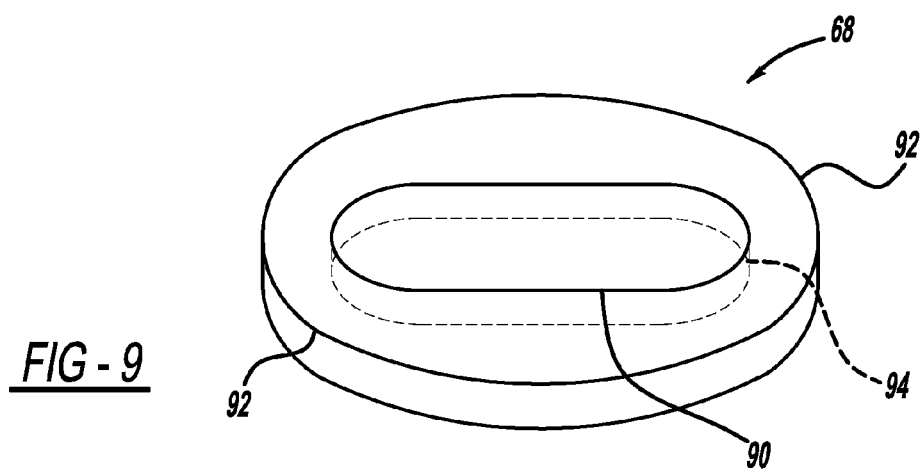
FIG. 9 is a perspective view of an insert of an acetabular implant according to various principles of the present disclosure.
Figure 8:
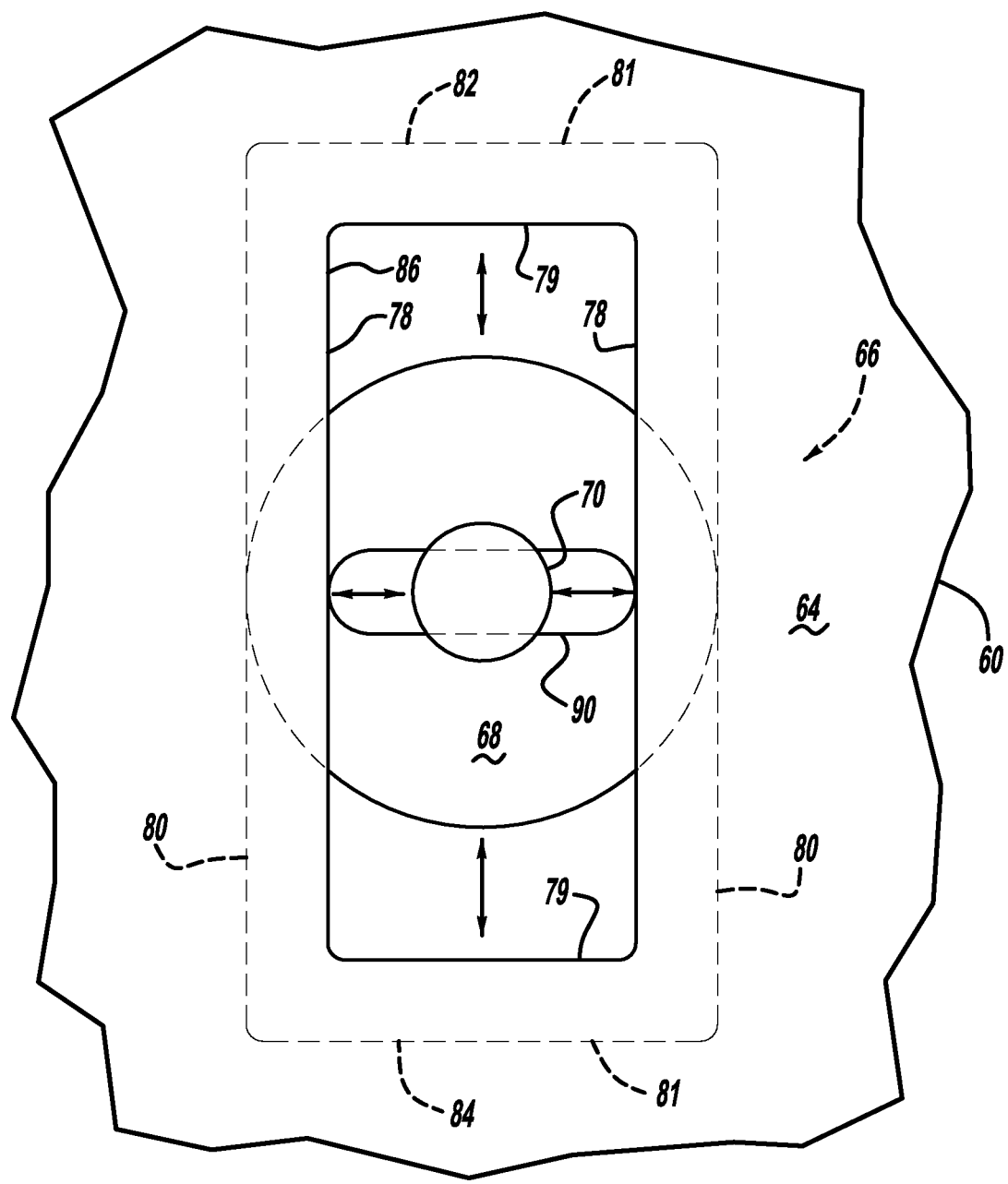
FIG. 8 is a perspective view of an acetabular implant according to various principles of the present disclosure.

FIGS. 7-10 illustrate another exemplary embodiment of an acetabular cup according to the present disclosure. Acetabular cup 60 illustrated in FIG. 7 is similar to acetabular cup 12 illustrated in FIGS. 1-6. In particular, acetabular cup 60 can be a hemispherically-shaped member having an exterior surface 62 that can engage with the acetabulum 13 of a patient, and an interior surface 64 that can interact with a prosthetic femoral head (not shown) of a prosthetic hip or a natural femoral head. Acetabular cup 60 can be formed of a material such as titanium, or any other material suitable for implantation into a patient that is known to one skilled in the art. In addition, acetabular cup 60 may include a coating or liner (not shown) formed on or positionable in an interior surface 64 made of a material such as polyethylene. Such a coating can improve the lubricity and cushioning characteristics between the prosthetic femoral head (not shown) and acetabular cup 60. A diameter of acetabular cup 60 can range between 40 mm and 80 mm, inclusive.

In place of aperture 22, acetabular cup 60 includes an elongated slot 66 that can be configured to receive an insert 68. The slot 66 is formed in a wall of the acetabular cup 60 between the interior surface 64 and the exterior surface 62. As slot 66 is operable to receive insert 68, slot 66 is elongated relative to a length of insert 68, which allows insert 68 to be in through slot 66 before insert 68 and acetabular cup 60 are fixed to the acetabulum 13 of the patient by fastener 70. A length of slot 66 can range between 10 mm and 70 mm, inclusive and also be defined as an arc length. Slot 66 can be formed at a center 72 of acetabular cup 60. Slot 66, however, can also be formed at positions radially outward from center 72, without departing from the scope of the present disclosure.

Slot 66 includes an upper surface 74 near or adjacent interior surface 64, and a lower surface 76 near or adjacent exterior surface 62. Slot 66 can also include aligned side surfaces 78, 79, 80, and 81. Insert 68 is slidable between opposing ends 82 and 84 defined by side surfaces 80 and 81. Slot 66 can include a pair of apertures 86 and 88. First aperture 86 is formed in interior surface 64 and second aperture 88 is formed in exterior surface 62. Although slot 66 is designed to retain insert 68 between upper surface 74 and lower surface 76, it should be understood that an alternative configuration can omit lower surface 76. In such a configuration, insert 68 would be aligned with slot 66 at exterior surface 62 before implantation of acetabular cup 60 into the patient. Although lower surface 76 can be omitted, insert 68 may remain movable within slot 66 before being secured in the acetabulum 13 along with cup 60.

Insert 68, as noted above, is slidable within slot 66. To ensure that insert 68 is not removable from slot 66, acetabular cup 60 can be formed from a pair of half-portions that are subsequently welded or brazed together after insert 66 is placed therebetween. Alternatively, if acetabular cup 60 is formed as a unitary member, insert 68 can be formed of a flexible material that can be manipulated into slot 66. Polymer materials that can be used to form insert 68 include polyethylene, polyether ether ketone (PEEK), and polyurethane. Alternatively, insert 68 can be formed from metal materials such as titanium and $Ti_6Al_4V$. Regardless, it should be understood that insert 68 is movable within slot 66 to a position that corresponds to the optimal position at which to secure fastener 70 to the acetabulum 13 of the patient. That is, insert 68 can be moved along slot 66 to a position that best corresponds to the optimum position of the acetabular anatomy where fastener 70 should secure acetabular cup 60 to the acetabulum 13. Once this position is located, fastener 70 may be tightened to secure insert 68 and acetabular cup 60 to the acetabulum 13 of the patient.

Figure 10:
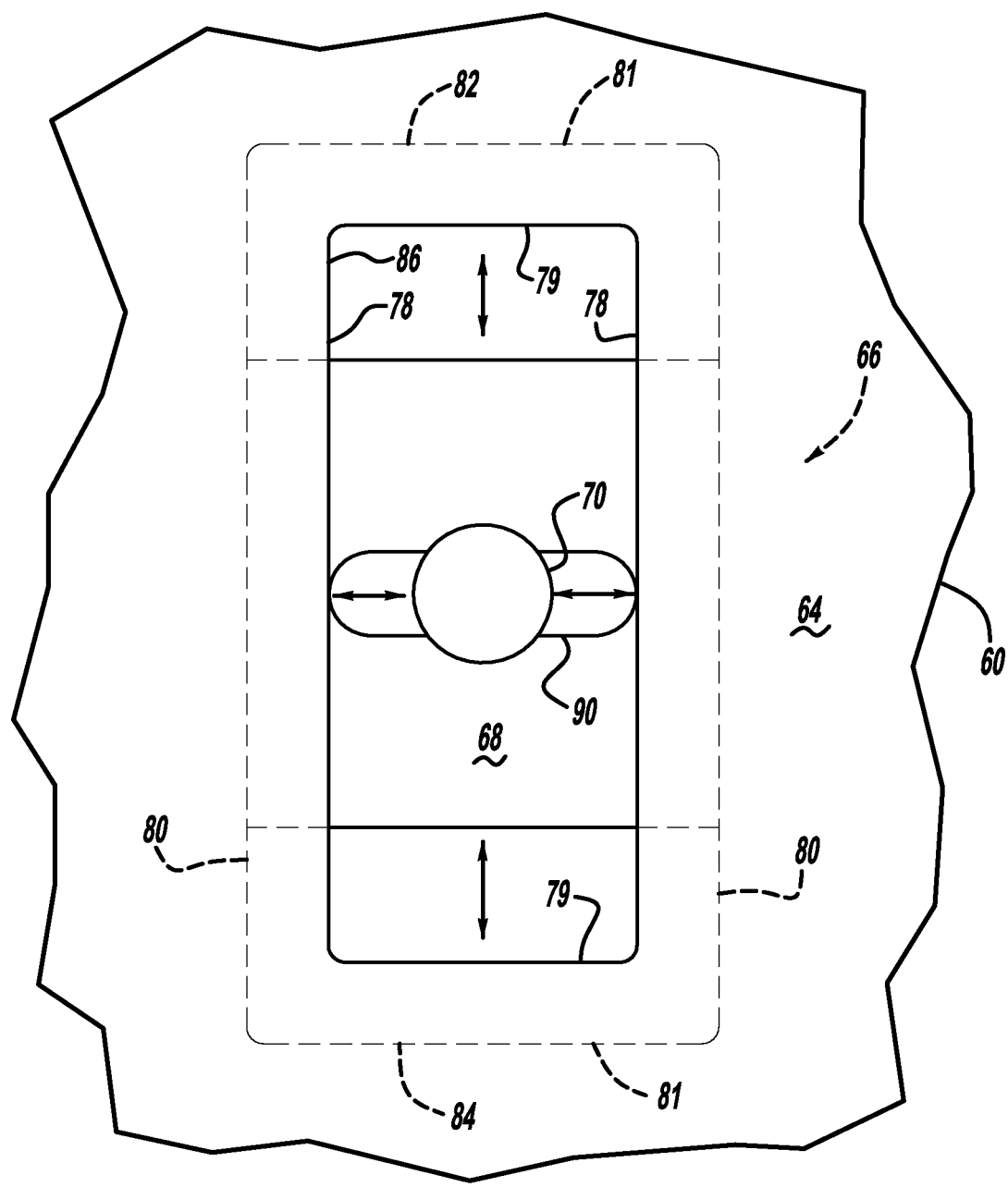
FIG. 10 is a perspective view of an acetabular implant according to various principles of the present disclosure.

To further increase the number of positions at which fastener 70 can secure insert 68 and acetabular cup 60 to the acetabulum 13 of the patient, insert 68 can also include a slot 90. Slot 90 can be positioned transverse to an extending direction of slot 66 or can be positioned at other angles relative to the extending direction of slot 66, and allows fastener 70 to be placed at additional positions that may correspond to the optimal position for fastener 70 to engage the acetabular anatomy of the patient. To position slot 90 at angles other than those transverse to slot 66, insert 68 may be rotatable through slot 66. Insert 68, although disc-shaped, is not necessarily circular. Insert 68, rather, can include truncated ends 92 (FIG. 9) to provide insert 68 with a substantially oval shape that prevents insert 68 from completely rotating in slot 66. Alternatively, as shown in FIG. 10, insert 68 can be square- or rectangular-shaped.

Slot 90 can have a length substantially equal to a width of apertures 86 and 88 of acetabular cup 60. Additionally, slot 90 can have tapered sidewalls 94 similar to through-hole 42 of insert 14 that engage with a tapered surface of fastener 70. In this regard, fastener 70 may be the same as fastener 16, described above. That is, fastener 70 can be a bone screw having a threaded shank 44 and a head 46 having a tapered surface 50. Alternatively, fastener 70 can be a bone screw that can be secured to acetabular cup 60 and insert 68 by a securing nut (not shown), without limitation.

After acetabular cup 60 is positioned in the acetabulum 13 of the patient, insert 68 can then be moved within slot 66 to a position that corresponds to an optimal or other selected position to secure fastener 70 to the acetabulum 13 of the patient. Once this position is located, fastener 70 may then be moved through slot 90 of insert 68 to an even more optimal position of the acetabular anatomy for securing the acetabular cup 60, and then tightened to secure insert 68 and acetabular cup 60 to the acetabulum 13 of the patient.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. For example, although insert 68 has been described above as having a slot 90, it should be understood that insert 14 may also include a slot. Further, acetabular cup 12 can include a slot 66 in lieu of aperture 22. Further, the insert according to various principles is operable to provide a moveable passage for the fastener 16 to be positioned through the acetabular cup 10, 60. Thus, fastener passages through the acetabular cup are not limited to limited positions of a single passage through the acetabular cup. Such variations are not to be regarded as a departure from the disclosure, and all such modifications are intended to be included within the scope of the disclosure.

What is claimed is:

1. An acetabular implant, comprising:
   an acetabular cup having an interior surface and an exterior surface, and an elongated aperture defined by a first longitudinal sidewall that connects the interior surface and the exterior surface;
   an insert engageable with the elongated aperture, the insert including a first insert sidewall that is sloped to correspond to a slope of the first longitudinal sidewall, wherein the elongated aperture is elongated relative to a length of the insert such that the insert is configured to be movable along a length of the elongated aperture; and
   a fastener that secures the insert to the acetabular cup, and is configured to directly secure the implant to an acetabulum of a patient.

2. The acetabular implant of claim 1, wherein the insert includes a through-hole having a first tapered surface, and the fastener includes a second tapered surface that corresponds to the first tapered surface of the through-hole.

3. The acetabular implant of claim 2, wherein the fastener includes a screw having a threaded shank, and a head that includes the second tapered surface.

4. The acetabular implant of claim 3, wherein engagement between the first longitudinal sidewall and the first insert sidewall, and engagement between the first tapered surface and the second tapered surface, secures the insert to the acetabular cup; and the threaded shank is configured to directly secure the implant to the acetabulum of a patient.

5. The acetabular implant of claim 1, wherein the insert is rectangular-shaped.

6. The acetabular implant of claim 1, wherein the first longitudinal sidewall and the first insert sidewall are sloped at an angle between 2 degrees and 20 degrees.

7. The acetabular implant of claim 1, wherein the insert is formed of materials selected from the group consisting of titanium, polyethylene, polyether ether ketone, polyurethane, and $Ti_6Al_4V$.

8. The acetabular implant of claim 1, further comprising:
   a second longitudinal sidewall that connects the interior surface and the exterior surface; and
   wherein the insert further comprises a second insert sidewall that is sloped to correspond to a slope of the second longitudinal sidewall.

9. The acetabular implant of claim 8, wherein the second longitudinal sidewall and the second insert sidewall are sloped at an angle between 2 degrees and 20 degrees.

10. The acetabular implant of claim 2, further comprising:
    a second longitudinal sidewall that connects the interior surface and the exterior surface; and
    wherein the insert further comprises a second insert sidewall that is sloped to correspond to a slope of the second longitudinal sidewall.

11. The acetabular implant of claim 10, wherein engagement between the first longitudinal sidewall and the first insert sidewall, engagement between the second longitudinal sidewall and the second insert sidewall, and engagement between the first tapered surface and the second tapered surface, secures the insert to the acetabular cup, and the threaded shank is configured to directly secure the implant to the acetabulum of a patient.

12. An acetabular implant, comprising:
   an acetabular cup including:
      an interior surface,
      an exterior surface, and
      an elongated aperture including an aperture longitudinal axis along an elongated aperture length, a first longitudinal sidewall and a second longitudinal sidewall, wherein the first and second longitudinal sidewalls connect the interior surface and the exterior surface;
   an insert engageable with the elongated aperture, the insert including:
      a first insert sidewall that is sloped to correspond to a slope of the first longitudinal sidewall,
      a second insert sidewall that is sloped to correspond to a slope of the second longitudinal sidewall, and
      an insert length defining an insert longitudinal axis, wherein the elongated aperture is elongated relative to the insert length such that the insert is configured to be movable along the aperture longitudinal axis; and
   a fastener that secures the insert to the acetabular cup, and is configured to directly secure the implant to an acetabulum of a patient.

13. The acetabular implant of claim 12, wherein the insert is rectangular shaped, such that the insert length is longer than an insert width.

14. The acetabular implant of claim 12, wherein each of the first and second longitudinal sidewalk and the first and second insert sidewalls is sloped at an angle between 2 degrees and 20 degrees.

15. An acetabular implant, comprising:
   an acetabular cup defining an elongated aperture having an aperture longitudinal axis along a length of the elongated aperture;
   an insert engageable with the acetabular cup at the elongated aperture, the insert defining an insert longitudinal axis, wherein the elongated aperture is elongated relative to the insert along the insert longitudinal axis such that the insert is configured to be movable along the length of the aperture; and
   a fastener configured to engage the insert and an acetabulum of a patient, such that the insert is secured relative to the acetabular cup and the implant is secured relative to the acetabulum of the patient.

16. The acetabular implant of claim 15, wherein the insert includes a through-hole having a first tapered surface, and the fastener includes a second tapered surface that corresponds to the first tapered surface of the through-hole.

17. The acetabular implant of claim 16, wherein the fastener includes a screw having a threaded shank, and a head that includes the second tapered surface.

18. The acetabular implant of claim 17, wherein:
   the acetabular cup includes an interior surface, an exterior surface, and a first longitudinal sidewall that connects the interior surface and the exterior surface;
   the elongated aperture is defined by the first longitudinal sidewall;
   the insert includes a first insert sidewall that is sloped to correspond to a slope of the first longitudinal sidewall; and
   engagement between the first longitudinal sidewall and the first insert sidewall, and engagement between the first tapered surface and the second tapered surface, secures the insert to the acetabular cup, and the threaded shank is configured to directly secure the implant to the acetabulum of a patient.

19. The acetabular implant of claim 15, wherein the insert is rectangular-shaped.

\* \* \* \* \*

UNITED STATES PATENT AND TRADEMARK OFFICE
CERTIFICATE OF CORRECTION

PATENT NO. : 9,744,046 B2
APPLICATION NO. : 13/754239
DATED : August 29, 2017
INVENTOR(S) : Meridew et al.

Page 1 of 1

It is certified that error appears in the above-identified patent and that said Letters Patent is hereby corrected as shown below:

In the Claims

In Column 6, Line 40, in Claim 4, delete "cup;" and insert --cup,-- therefor

In Column 7, Line 36, in Claim 14, delete "sidewalk" and insert --sidewalls-- therefor Signed and Sealed this
Twenty-eighth Day of May, 2019

Andrei Iancu
*Director of the United States Patent and Trademark Office*